United States Patent [19]

Koichi et al.

[11] Patent Number: 4,935,352

[45] Date of Patent: Jun. 19, 1990

[54] EXPRESSION VECTOR FOR ANIMAL CELL LINE AND USE THEREOF

[75] Inventors: Igarashi Koichi, Kyoto; Sasada Reiko, Nagaokakyo; Fujii Tomoko, Toyonaka; Marumoto Ryuji, Ashiya, all of Japan

[73] Assignee: Takeda Chemical Industries, Ltd., Osaka, Japan

[21] Appl. No.: 919,798

[22] Filed: Oct. 16, 1986

[30] Foreign Application Priority Data

Oct. 21, 1985 [JP] Japan .................. 60-236189
Aug. 1, 1986 [JP] Japan .................. 61-182457

[51] Int. Cl.$^5$ .............. C12N 15/00; C12N 1/00; C12P 1/00
[52] U.S. Cl. ................... 435/69.52; 435/172.1; 435/172.3; 435/320; 435/240.1; 435/69.3; 435/69.4; 435/69.51; 435/69.8; 935/10; 935/11; 935/22; 935/49; 935/48
[58] Field of Search ............ 435/68, 172.3, 70, 91, 435/320, 240.1; 536/27

[56] References Cited

FOREIGN PATENT DOCUMENTS

| 89676 | 9/1983 | European Pat. Off. . |
| 121352 | 8/1984 | European Pat. Off. . |
| 170266/1985 | 7/1985 | European Pat. Off. . |
| 177915 | 4/1986 | European Pat. Off. . |
| 61-57919 | 3/1986 | Japan . |
| 61-82699 | 4/1986 | Japan . |
| 61-231428 | 9/1986 | Japan . |
| 61-241053 | 10/1986 | Japan . |

OTHER PUBLICATIONS

Watson et al., (1984), Nucleic Acids Res., 12:5145-5165.
Hood et al., eds., Immunology, p. 63, (1978), Benjamin/Cummings Publ. Co. Inc.
Crowley et al., Mol. Cell Biol., 3:44-55, (1983).
Bitter et al., Proc. Natl. Acad. Sci. U.S.A., 81:5330-5334, (1984).
Miyajima et al., Gene, 37:155-161, (1985).
Brake et al., Proc. Natl. Acad. Sci. U.S.A., 81:4642-4646, (1984).
Ghrayeh et al., Embo J., 3:2437-2442, (1984).
Palva et al., Gene, 22:229-235, (1983).
Bernard Davis et al., Nature, 283, 433, (1980).
Daniel Perlman et al., J. Mol. Biol., 167, 391, (1983).
Tadatsugu Taniguchi et al., Nature, 302, 305, (1983).
Patrick Gray et al., Nature, 295, 503, (1982).
Science, 221:236, (1983).
Nucleic Acids Res., 11:719, (1983).

*Primary Examiner*—Robin L. Teskin
*Assistant Examiner*—Anne Brown
*Attorney, Agent, or Firm*—David G. Conlin; Ronald I. Eisenstein

[57] ABSTRACT

An animal cell line transformed with an expression vector for an animal cell, the expression vector which contains a DNA segment comprising:

(a) a DNA sequence coding for a signal peptide of an animal cell-derived protein,
(b) a second DNA sequence coding for a different protein from the signal protein joined downstream of said signal peptide encoding DNA sequence without causing any reading frame shift, and
(c) a promoter DNA sequence capable of functioning in an animal cell, wherein the promoter sequence is positioned upstream of the signal peptide encoding DNA sequence, can produce glycosylated proteins advantageously as secretable proteins.

13 Claims, 7 Drawing Sheets

Fig. 1

5' GGGGGGGGGGGGGGGGGATCACTCTCTTTAATCACTACTCACAGTAACC

Pst I

S1
TCAACTCCTGCCACA ATG TAC AGG ATG CAA CTC CTG TCT TGC

S20   1
ATT GCA CTA AGT CTT GCA CTT GTC ACA AAC AGT GCA CCT
                                             Hgi AI

ACT TCA AGT TCT ACA AAG AAA ACA CAG CTA CAA CTG GAG
                        20              Alu I

CAT TTA CTG CTG GAT TTA CAG ATG ATT TTG AAT GGA ATT

40
AAT AAT TAC AAG AAT CCC AAA CTC ACC AGG ATG CTC ACA

TTT AAG TTT TAC ATG CCC AAG AAG GCC ACA GAA CTG AAA
                  60
CAT CTT CAG TGT CTA GAA GAA GAA CTC AAA CCT CTG GAG

80
GAA GTG CTA AAT TTA GCT CAA AGC AAA AAC TTT CAC TTA
             Alu I

AGA CCC AGG GAC TTA ATC AGC AAT ATC AAC GTA ATA GTT
                           100
CTG GAA CTA AAG GGA TCT GAA ACA ACA TTC ATG TGT GAA

TAT GCT GAT GAG ACA GCA ACC ATT GTA GAA TTT CTG AAC
120
AGA TGG ATT ACC TTT TGT CAA AGC ATC ATC TCA ACA CTG
133
ACT TGA TAATTAAGTGCTTCCCACTTAAAACATATCAGGCCTTCTATTT
                                           Stu I
ATTTAAATATTTAAATTTTACCCCCCCCCCCCCCC 3'
                                Pst I

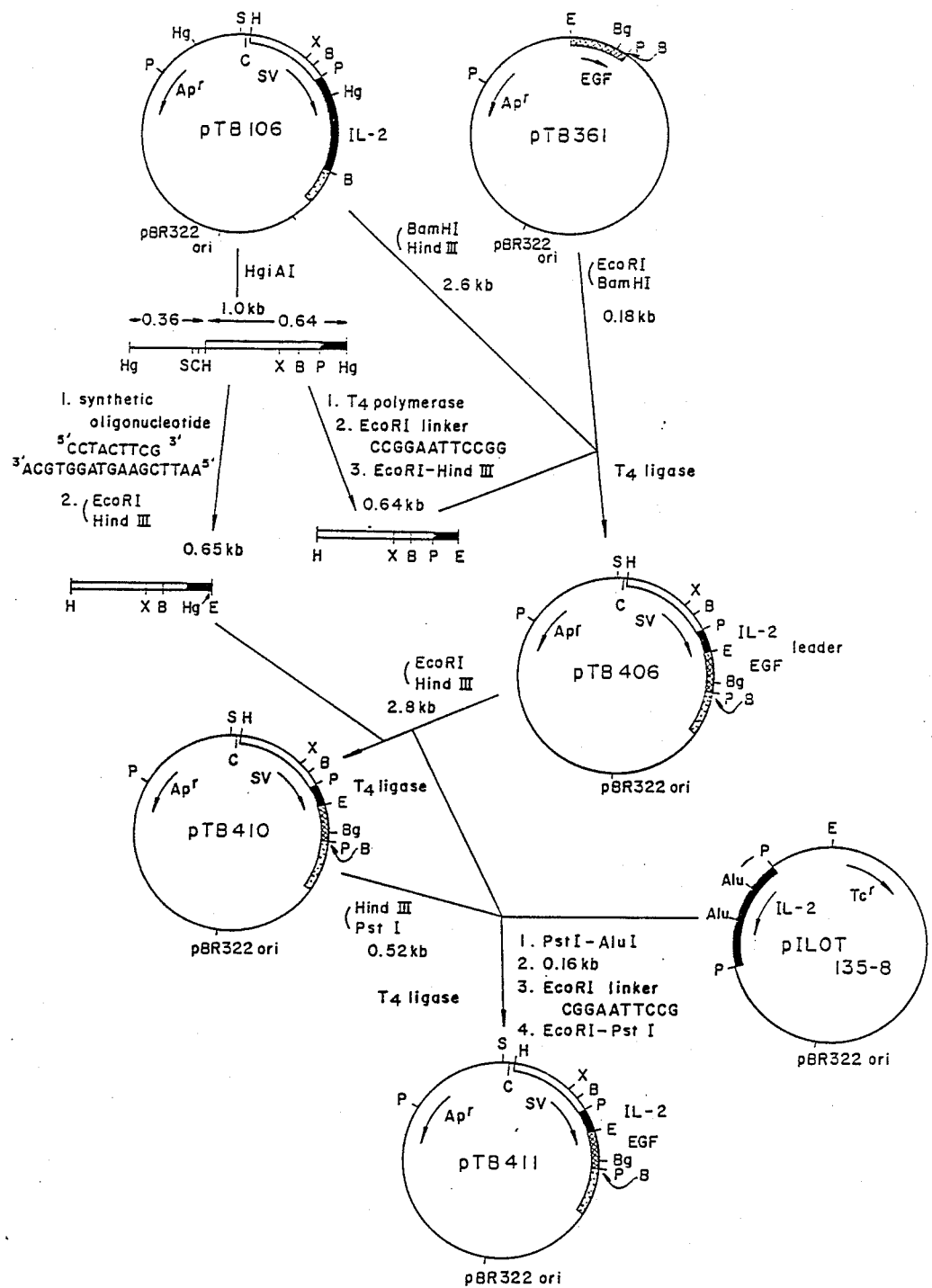

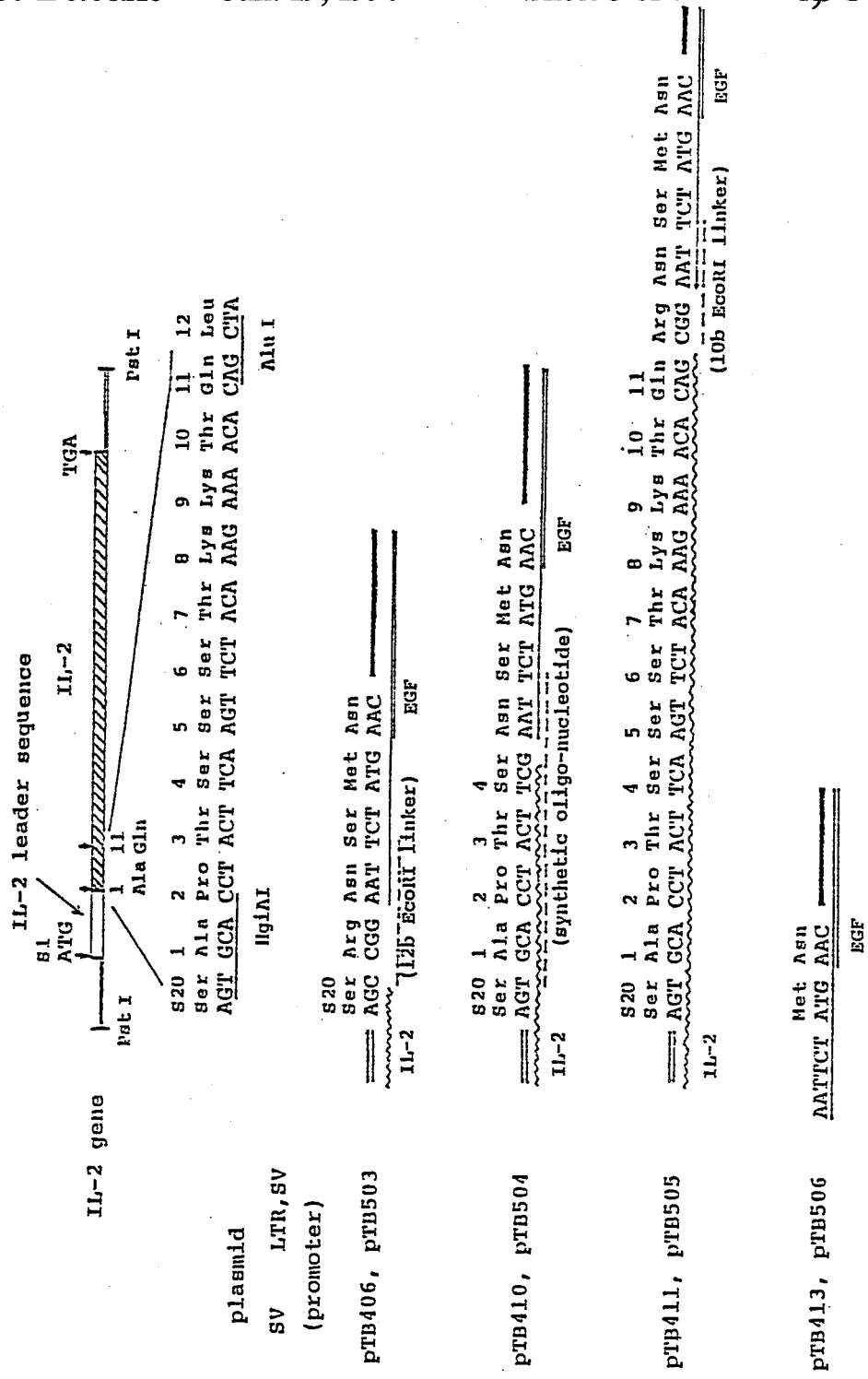

EXPRESSION VECTOR FOR ANIMAL CELL LINE AND USE THEREOF

The present invention relates to an expression vector for animal cell line and use thereof.

Proteins to be extracellularly secreted after their synthesis within cells (proteins which are secreted from cells through the cell membrane) must permeate the cell membrane in the process of their secretion. To permeate the hydrophobic membrane, binding of the ribosome to the endoplasmic reticulum is first required for these secretory proteins, which are generally water soluble. Secretory proteins are generally synthesized within cells in the form of preproteins having an additional peptide sequence (called "signal peptide"). It is believed that this signal peptide functions as the signal for inducing the ribosome to bind to the endoplasmic reticulum. It is expected that receptors recognizing preproteins naturally occur on the endoplasmic reticulum. Upon synthesis thereof, preproteins pass through the endoplasmic reticulum with the signal peptide at the head. At this time, the signal peptide is cleaved away by the action of a membrane-related endopeptidase called signal peptidase and final, hydrophilic, mature proteins having a folded structure are secreted into the cavity of the endoplasmic reticulum. These proteins are sent out extracellularly via the Golgi apparatus [Nature, 283: 433 (1980)].

The signal peptide of a secretory protein generally differs in primary structure from one protein to another to a considerable extent although there is some partial similarity from protein to protein [J. Mol. Biol., 167 391 (1983)]. This is considered to be a result of the evolution of signal peptides so that the respective proteins can be secreted successfully.

Therefore, even when a useful gene coding for a mature protein is used without leader sequence in an expressible form for the expression of said gene in animal cells, the protein synthesized accumulates within the cell but is not secreted into the cell culture medium. Thus, in such case, it is necessary to use said gene in the form having a DNA (leader sequence) coding for the signal peptide to the protein in question as added to the 5' end thereof. However, for many genes, the leader sequence remains unknown. In addition, when, as in the case of epithelial growth factor (EGF) [Science, 221: 236 (1983)], the desired protein is produced from a very small C-terminal portion of a huge mature protein by processing, it is very difficult to obtain a cDNA containing the leader sequence to the 5' end thereof by cDNA synthesis based on the messenger RNA, since the RNA is huge. Furthermore, even where a gene can be chemically synthesized based on the primary structure of a known protein where the gene structure itself is unknown, for use in large-scale production thereof, the protein will not be expressed in the secretable form in animal cells but will be accumulated within cells since the leader sequence is unknown. This means that the yield of the desired protein is decreased by an extreme extent, and that much labor and time are required for the extraction of the protein from cells and for the recovery thereof in a purified form from the extract by purification and that, in extreme cases, it is very difficult to obtain the desired substance itself in a complete and pure form.

Thus far it has been almost impossible to obtain expression of a gene, for which the leader sequence is unknown or which can be obtained only with much difficulty, in a secretable form in animal cells. The present inventors have found that the product of such a gene can be efficiently secreted from animal cells and accumulated in the culture medium by using a leader sequence originally not inherent to the cellular gene. As a result of further research, the present invention has now been completed.

The invention provides:

(1). An expression vector which contains a DNA segment comprising:

(a) a DNA sequence coding for a signal peptide of an animal cell-derived protein, (b) a second DNA sequence coding for a different protein from the signal protein joined downstream of said signal peptide encoding DNA sequence without causing any reading frame shift, and (c) a promoter DNA sequence capable of functioning in an animal cell, wherein the promoter sequence is positioned upstream of the signal peptide encoding DNA sequence;

(2) A method for producing a DNA segment of an expression vector for use in an animal cell, which comprises constructing a DNA segment comprising (a) a DNA sequence coding for a signal peptide of an animal cell-derived protein, (b) a DNA sequence coding for a different protein from the signal protein encoding DNA sequence, and (c) a promoter DNA capable of functioning in an animal cell, in the order that the signal protein encoding DNA sequence is upstream of the protein-encoding DNA sequence and the promoter DNA is upstream of the signal peptide encoding DNA sequence;

(3). An animal cell line transformed with an expression vector which contains a DNA segment comprising:

(a) a DNA sequence coding for a signal peptide of an animal cell-derived protein, (b) a second DNA sequence coding for a different protein from the signal protein joined downstream of said signal peptide encoding DNA sequence without causing any reading frame shift, and (c) a promoter DNA sequence capable of functioning in an animal cell, wherein the promoter sequence is positioned upstream of the signal peptide encoding DNA sequence;

(4). A method for producing an animal cell line, which comprises transforming an animal cell line with an expression vector which contains a DNA segment comprising:

(a) a DNA sequence coding for a signal peptide of an animal cell-derived protein, (b) a second DNA sequence coding for a different protein from the signal protein joined downstream of said signal peptide encoding DNA sequence without causing any reading frame shift, and (c) a promoter DNA sequence capable of functioning in an animal cell, wherein the promoter sequence is positioned upstream of the signal peptide encoding DNA sequence; and (5). A method of producing a protein, which comprises cultivating in a medium an animal cell transformed with an expression vector for an animal cell, the expression vector which contains a DNA segment comprising:

(a) a DNA sequence coding for a signal peptide of an animal cell-derived protein, (b) a second DNA sequence coding for a different protein from the signal protein joined downstream of said signal peptide encoding DNA sequence without causing any reading frame shift, and (c) a promoter DNA sequence capable of functioning in an animal cell, wherein the promoter sequence is positioned upstream of the signal peptide encoding DNA sequence, and collecting the protein thus secreted and accumulated in the medium.

The protein-encoding DNA (gene) to be used for secretory expression is more preferably one for which the base sequence is known and may be a gene isolated from a chromosome, a cDNA synthesized on the basis of a messenger RNA (mRNA), a chemically synthesized gene or any other gene. More particularly, it includes genes coding for a variety of physiologically active proteins, for example the genes coding for cytokines such as interferons (IFNs; e.g. IFN-$\alpha$, IFN-$\beta$, IFN-$\gamma$), interleukins (e.g. interleukin-1, interleukin-2), B cell growth factor (BGF), B cell differentiation factor (BDF), macrophage activating factor (MAF), lymphotoxin (LT) and tumor necrosis factor (TNF); for transforming growth factor (TGF-$\alpha$); for peptide protein hormones such as erythropoietin, fibroblast growth factor (FGF), epithelial cell growth factor (EGF), insulin and human growth hormone; for pathogenic bacteria-derived antigenic proteins such as hepatitis B virus antigen, influenza antigen, foot-and-mouth disease virus antigen and malarial protozoan antigen; for enzymes such as peptidases (e.g. tissue plasminogen activator, urokinase, serrapeptase) and lysozyme; and for blood protein components such as human serum albumin HSA). immunoglobulin proteins (e.g. IgG, IgE). Among them, hepatitis B virus gene (Japanese Patent Laid-open No. 209298/1982, which corresponds to European Patent Publication No. 68719), the immunoglobulin E gene [Nucleic Acids Res., 11: 719 (1983)], the immune interferon (IFN-$\gamma$) gene (Japanese Patent Laid-open No. 189197/1983, which corresponds to European Patent Publication No. 89676), the human epithelial cell growth factor (EGF) gene (Japanese Patent Application No. 210502/84, filed Oct. 9, 1984, which corresponds to European Patent Publication No.177915), and the human fibroblast growth factor (FGF) gene (Japanese Patent Application No. 82699/1986, filed Apr. 9, 1986) are particularly preferred. Either the whole or a sufficient part of the structural gene coding for such a protein may be used.

In constructing plasmids for secretory expression by inserting a gene such as mentioned above into an expression vector at a site downstream from the leader sequence, for instance, it is also possible to join an appropriate synthetic oligonucleotide to the gene as necessary.

The DNA sequence coding for the signal peptide of a different, animal cell-derived protein is a DNA sequence coding for the signal peptide of an animal cell-derived protein different from the protein in relation to the above-mentioned gene and includes, among others, those DNA sequences coding for the signal peptides of human interleukin-2 (IL-2) (Japanese Patent Laid-open No. 115528/1985, which corresponds to European Patent Publication No. 145390), IFN-$\gamma$ (Japanese Patent Laid-open No. 189197/1983, which corresponds to European Patent Publication No. 89676), human tumor necrosis factor (TNF) [Nature, 312: 724 (1984)] and human lymphotoxin (LT) [Nature, 312: 721 (1984)].

A preferred example of such DNA sequence is a sequence coding for the signal peptide of IL-2 which has the formula Met Tyr Arg Met Gln Leu Leu Ser Cys Ile (I)
Ala Leu Ser Leu Ala Leu Val Thr Asn Ser and the leader sequence of IL-2 which has the formula GCA CCT ACT TCA AGT TCT ACA AAG AAA ACA (II)
CAG CTA CAA CTG GAG CAT TTA CTG CTG GAT is particularly preferred.

The above-mentioned DNA sequence coding for the signal peptide of a protein may have, at the 3' terminus thereof, a DNA coding 1 to about 20 amino acids of the N-terminal polypeptide of the protein.

The DNA sequence according to the invention which codes for the signal peptide of a different, animal cell-derived protein can be produced as a cDNA (leader sequence) synthesized based on an mRNA or as a DNA sequence derived chemically by half synthesis [Tetrahedron Letters, 22: 1859 (1981)] or total synthesis using a per se known method, for example the phosphorous amide method.

In producing the leader sequence for a protein on the basis of an mRNA, a plasmid containing the leader sequence DNA for the protein can be produced, for example by (a) isolating the mRNA coding for the animal cell-derived protein, (b) synthesizing a single-stranded cDNA based on said RNA and then a double-stranded DNA, (c) inserting said cDNA into a plasmid, (d) transforming a host with the recombinant plasmid obtained, (e) cultivating the transformant obtained, then isolating the plasmid containing the leader sequence for the protein from the transformant, (f) excising the desired, cloned leader sequence DNA from the plasmid, and (g) inserting the cloned DNA into a vehicle at a site downstream from a promoter in the vehicle This plasmid can be introduced into an appropriate host, for example *Escherichia coli*. From among the transformants obtained in this manner, the desired clone can be picked out by a conventional method, for example by colony hybridization. This series of basic procedures is known in the art and described in detail in Methods in Enzymology, 68 (1979) and Molecular Cloning (1982), Cold Spring Harbor Laboratory.

After plasmid production from the above transformant by a conventional method, the leader sequence DNA can be isolated by a conventional method, for example by cleaving the plasmid with a restriction enzyme, followed by polyacrylamide gel electrophoresis or agarose gel electrophoresis, for instance The base sequence of the DNA fragment isolated can be determined by conventional method, for example by the dinucleotide synthesis chain termination method [Proc Natl. Acad. Sci. USA, 74: 5463 (1977)].

The promoter to be used in the practice of the invention is capable of functioning in animal cells and may be any promoter provided that it is competent and suited for the host to be used for gene expression. There may be mentioned, for example, the SV40-derived promoter and a retrovirus-derived promoter, which are suitable for expression in monkey cell lines COS-7 and vero, chinese hamster cell line CHO and mouse cell line L, among others.

The expression vector for use in animal cells according to the present invention can be produced, for example by inserting a DNA segment comprising (a) a DNA sequence coding for a signal peptide of an animal cell-derived protein, (b) a second DNA sequence coding for a different protein from the signal protein joined downstream of said signal peptide encoding DNA sequence without causing any reading frame shift, and (c) a promoter DNA sequence capable of functioning in an animal cell, wherein the promoter sequence is positioned upstream of the signal peptide encoding DNA sequence, into a known vector, such as pBR322, using a restriction enzyme or enzymes and ligase to thereby construct said vector.

The transformed animal cells according to the invention can be produced by transforming animal cells with the above-mentioned expression vector for animal cells, as necessary followed by cloning or harvesting.

The above animal cells may be any cells capable of allowing expression of the leader sequence for the protein. Examples are mouse cells (e.g. L cells, Balb/3T3 cells), human cells (e.g. FL cells) and hamster cells (e.g. CHO cells)

The transformation is advantageously effected by cotransfection [Cell, 16: 777 (1979)], for instance, whereby the desired animal cell transformant can be cloned and isolated.

The method of producing desired proteins in accordance with the invention can be carried out by cultivating the above transformed animal cells to thereby cause secretion and accumulation of a desired protein in the medium and collecting the protein.

The cultivation of animal cells is conducted in a conventional medium for animal cell culture, for example in MEM medium containing about 5 to 20% of fetal calf serum, at about 30° to 40° C. for about 1 to 10 days.

The desired protein produced and accumulated in the medium may be used in the form of a culture broth concentrate after removal of the cells and subsequent concentration to dryness. Alternatively, the desired protein can be isolated and purified from the culture supernatant by an appropriate combination of conventional separation and purification methods.

By using specific transformants in accordance with the invention, glycosylated proteins can be produced mainly as secretable proteins.

The method of producing proteins according to the invention using animal cell transformants allows easy and large-scale production of glycosylated proteins when such proteins are desired. In this case, the glycosylated proteins can be purified and utilized favourably since they are stable and highly soluble in water because of their being glycosylated as compared with those proteins produced in *Escherichia coli* or the like by recombinant DNA techniques and further since they have been secreted into the medium.

The glycosylated proteins produced in accordance with the invention have physiological activities equivalent to those of the corresponding known proteins and can be used as drugs, etc. They can be used in the same manner as the known proteins.

Furthermore, an animal cell line, transformed with an expression vector of the present invention which expresses a cell growth factor gene (e.g. genes of EGF, TGF, FGF) for an animal cell, produces said cell growth factor continuously, and therefore, it causes the same effect to the cell as when a cell growth factor is separately added. It is observed that in the cultivation of said transformant cell, the proliferation rate is increased and the demand for serum is decreased. This is very advantageous for the enhanced production of a useful substance when the present invention is used with a useful substance producing cell line or transformant cell line.

BRIEF DESCRIPTION OF THE DRAWINGS

FIG. 1 shows the base sequence of the IL-2 leader sequence and structural gene portion contained in the plasmid pILOT135-8.

FIG. 2 shows the construction scheme for the plasmids pTB406, pTB410 and pTB411.

FIG. 3 shows the base sequence of a particular and characteristic portion of each of several EGF expression vectors.

Figure 4:
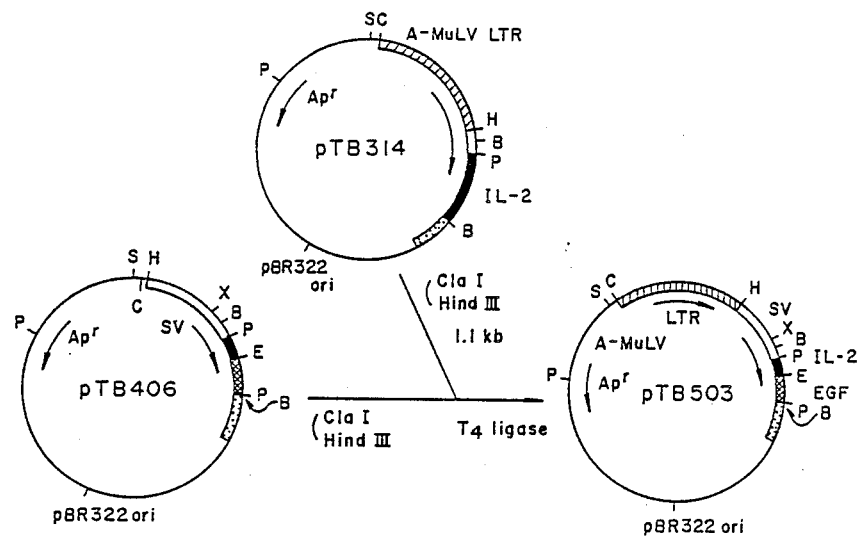
FIG. 4 shows the construction scheme for the plasmid pTB503.

In the figures, the restriction enzyme cleavage sites are abbreviated as follows:

B for BamHI, Bg for BglII, C for ClaI, E for EcoRI,
H for HindIII, S for SalI, X for XhoI, P for PstI,
Hg for HgiAI and Alu for AluI.

In the present specification and the accompanying drawings, the bases and so forth, when given in terms of abbreviations, are abbreviated in accordance with the recommendations of the IUPAC-IUB Commission on Biochemical Nomenclature or the practice conventional in the relevant field of art. The following is a listing of several examples.

DNA: Deoxyribonucleic acid
cDNA: Complementary deoxyribonucleic acid
A: Adenine
T: Thymine
G: Guanine
C: Cytosine
RNA: Ribonucleic acid

EXAMPLES

The following examples are further illustrative of the invention but the present invention is not to be limited to these examples.

The transformants disclosed herein have been deposited at the Institute for Fermentation, Osaka (IFO), Japan under the accession numbers:

Mouse LA9-IS11 EGF-2 cell: IFO-50057 (Deposit date: July 18, 1985)

Mouse L-IS11 IgE-9 cell: IFO-50056. (Deposit date: July 18, 1985)

Mouse A31-IS11EGF-2 cell: IFO-50093 (Deposit date: July 30, 1986)

EXAMPLE 1

(Expression vector for human EGF secretion and human EGF-producing animal cell transformants)

(i) Construction of the plasmids pTB406, pTB410 and pTB411

The IL-2 gene expression vector pTB106 for animal cells [Example 1-(i) in the specification of Japanese Patent Application No. 133490/85 (filed June 18, 1985) which corresponds to European Patent Publication No. 172619] was cleaved with the restriction enzyme HgiAI and a 1.0 kb DNA fragment containing the IL-2 gene leader sequence was isolated The cohesive ends were made blunt by T4 DNA polymerase reaction. Following addition of the EcoRI linker CCGGAATTCCGG using T4 DNA ligase, complete digestion with EcoRI and HindIII was performed and a 0.64 kb DNA fragment comprising an SV40 DNA-derived sequence (promoter and splicing site) and the IL-2 gene leader sequence was isolated. Separately, the above pTB106 was cleaved with BamHI and HindIII and a 2.6 kb DNA fragment comprising the DNA replication origin for the replication of pBR322-derived plasmids in *Escherichia coli*, a sequence containing the ampicillin resistance gene, and the SV40 DNA-derived poly-A addition site, was isolated. Also separately, a 0.18 kb EcoRI-BamHI DNA fragment coding for human EGF was produced from pTB361 [Example 4 in Japanese Patent Application No. 210502/1984 (filed Oct. 9, 1984, which corresponds to European Patent Publication No. 177915)] in which a synthetic human EGF gene has been cloned. The above three DNA fragments were joined together by T4 DNA ligase reaction to thereby construct pTB406. pTB406 has a structure comprising the leader sequence covering No. 1-123 nucelotides (FIG. 1) of the IL-2 gene DNA and the synthetic human EGF gene DNA as joined together by the intermediary of the EcoRI linker and the translation initiation codon ATG of the EGF DNA is inserted without causing any reading frame shift.

Then, the above-mentioned 1.0 kb DNA fragment obtained by cleavage of the plasmid pTB106 with HgiAI was mixed with the synthetic oligonucleotides 5'CCTACTTCG3' and 5'AATTCGAAGTAGGT-GCA3' each produced by methods well known in the art. The resulting mixture was subjected to reaction in the presence of T4 DNA ligase and the ligation product was cleaved with EcoRI and HindIII. A 0.65 kb EcoRI-HindIII DNA fragment was then isolated and purified. The thus-obtained DNA fragment has an SV40 DNA-derived sequence, and the whole IL-2 gene leader sequence and the base sequence coding for the four amino acids on the N-terminus side of the IL-2 protein molecule. Separately, the previously constructed pTB406 was cleaved with EcoRI - HindIII and a 2.8 kb DNA fragment containing the EGF gene, the poly-A addition site and the pBR322-derived sequence was isolated. This fragment was ligated with the abovementioned 0.65 kb EcoRI-HindIII DNA fragment to thereby construct pTB410.

Further, pILOT135-8 (Japanese Patent Laid-open No. 115528/1985, which corresponds to European Patent Publication No. 145390) was cleaved with PstI and AluI and a 0.16 kb DNA fragment having the sequence coding for the IL-2 gene leader sequence and the 11 amino acids on the N-terminus side of the IL-2 molecule was isolated. The EcoRI linker CGGAATTCCG was added to the blunt end resulting from AluI cleavage to construct a DNA fragment. This 0.16 kb fragment was ligated with the abovementioned 2.8 kb DNA fragment obtained by EcoRI-HindIII cleavage of pTB406 and a 0.52 kb DNA fragment obtained by HindIII-PstI cleavage of pTB410 by T4 DNA ligase reaction to thereby construct pTB411.

The construction schemes for these EGF expression vectors pTB406, pTB410 and pTB411 are shown in FIG. 2.

For each of these recombinants, the construction (base sequence and deduced amino acid sequence) of the linking site between the IL-2 leader sequence-containing region and the human EGF synthesis gene is shown in FIG. 3.

The IL-2 gene-derived sequence in pTB406 covers nucleotides Nos. 1-123, that in pTB410 Nos. 1-135, and that in pTB411 Nos. 1-158 (FIG. 1).

(ii) Construction of plasmids pTB503, pTB504 and pTB505

The human IL-2 leader sequence-containing human EGF expression vectors obtained in Example 1 (i), namely pTB406, pTB 410 and pTB411, were cleaved respectively at the ClaI and HindIII sites occurring upstream from the SV40 promoter, to which were inserted a 1.1 kb ClaI-HindIII DNA fragment separated and purified from pTB314 [Example 1 (iii) in the specification for Japanese Patent Application No. 133490/85 (filed June 18, 1985), which corresponds to European Patent Publication No. 172619] and containing the Abelson mouse leukemia virus (A-MuLV) LTR region. Thus were constructed pTB503, pTB504 and pTB505, respectively. These recombinants are expected to bring about high-efficiency expression of the gene as desired particularly in mouse cells. The construction scheme for pTB503 is shown in FIG. 4 by way of example.

(iii) Transformation of animal cells

Dulbecco's modified MEM (DMEM) medium containing 10% fetal calf serum was placed in Falcon dishes (6 cm in diameter) and HPRT (hypoxanthine phosphoribosyl transferase)-deficient mouse L cells (LA9 cells) [Littlefield, J. W., Exp. Cell Res., 41: 190-196 (1966)] were cultivated overnight at 37° C. Thereafter, these cells ($7 \times 10^5$ cells/dish) were cotransfected by incubation with a mixture of 0.5 μg of the plasmid p4aA8 (human HPRT cDNA-containing plasmid) [Jolly, D. J. et al., Proc. Natl. Acad. Sci. USA, 80: 477-481 (1983)] and 10 μg of the pTB505 DNA according to the method of Graham et al. [Virology, 52: 456-467 (1973)]. After cultivation at 37° C. for 4 hours, the medium was replaced with a fresh portion and cultivation was conducted overnight. On the next day, the medium was replaced with HAT medium (DMEM medium containing 15 μg/ml hypoxanthine, 1 μg/ml aminopterine and 5 μg/ml thymidine) containing 10% fetal calf serum and cultivation was continued at 37° C. The cultivation was continued with medium exchange at 3- to 4-day intervals. After about 2-3 weeks, cells, now HPRT+, multiplied to form colonies.

(iv) Cloning of transformants and assay of EGF

The transformed cells obtained in Example 1 (iii) were cloned by the limited dilution method. After completion of the cloning, the cloned cells were grown in DMEM medium containing 10% fetal calf serum. The cloned cells were picked up and sowed on Linbro dishes (Flow) and, when cells were about 80% confluent, the medium was replaced with a fresh portion. Two days later, the culture supernatant was assayed for EGF. The amount of EGF was determined by the radioreceptor assay (RRA) method [Cohen, S. et al., Proc. Natl. Acad. Sci. U.S.A., 72: 1317–1321 (1975)] and expressed in terms of the weight of purified mouse EGF standard showing the same level of activity. Thus, Flow 7000 human foreskin cells (commercially available from Flow, Inc.) were cultivated in Linbro dishes (1.6 cm in diameter) using DMEM medium containing 10% fetal calf serum. The medium was then discarded, the cells were washed with DMEM medium containing 0.1% BSA and, then, 0.2 ml of the same medium, 5 ng of mouse EGF (commercially available from Collaborative Research Inc.) labeled with $^{125}I$ by the chloramine T method and an adequate amount of the culture supernatant of the transformed cell clone obtained above were added. After cultivation at 37° C. for 1 hour, the cells were washed with the same medium, treated with 0.2 N NaOH, transferred to a tube and counted for the up take of $^{125}I$ with a gamma counter. The human EGF amount in the culture supernatant was calculated based on a working curve constructed by following the same procedure for conducting the reaction competitively with known weights of mouse EGF.

EGF was detected in quantities of 70–80 ng/ml in the LA9 transformant cell culture supernatants obtained The results obtained are shown in Table 1.

TABLE 1

| Plasmid | Transformant (clone) | EGF in culture supernatant, ng/ml |
|---|---|---|
| pTB505 | LA9-IS11 EGF-2 | 80 |
|  | LA9-IS11 EGF-3 | 70 |
| pTB506 (nonsecretory type control) | LA9-EGF-3 | <1 |

For the transformant clone mouse LA9-IS11 EGF-2 (IFO 50057), for which EGF had been detected in the culture supernatant, the content of EGF within cells was compared with that in the culture supernatant. Thus, LA9-IS11 EGF-2 cells were sown on Falcon dishes (6 cm in diameter) and, just before the cells became confluent, the medium was replaced with a fresh 5-ml portion. On the next day, the culture supernatant was sampled. At the same time, cells were scraped off with a rubber policeman and collected by centrifugation (2,000 rpm×5 minutes). After addition of 200 μl of 10 mM Tris-HCl (pH 7.5), the cells collected were disrupted by sonication (5 seconds×2) and then subjected to centrifugation (20,000 rpm, 4° C., 30 minutes), and the supernatant obtained was assayed for EGF activity by the method mentioned above. The previously sampled culture supernatant was also assayed for EGF in the same manner. As a result, it was found that the mouse LA9-IS11 EGF-2 cells had produced about 400 ng of EGF in the culture medium and about 75 ng of EGF in the cell extract, per $10^7$ cells, respectively Then, for the animal cell transformant LA9-IS11 EGF-2 obtained in Example 1 (iv), the culture supernatant was assayed for EGF at timed intervals.

Figure 5:
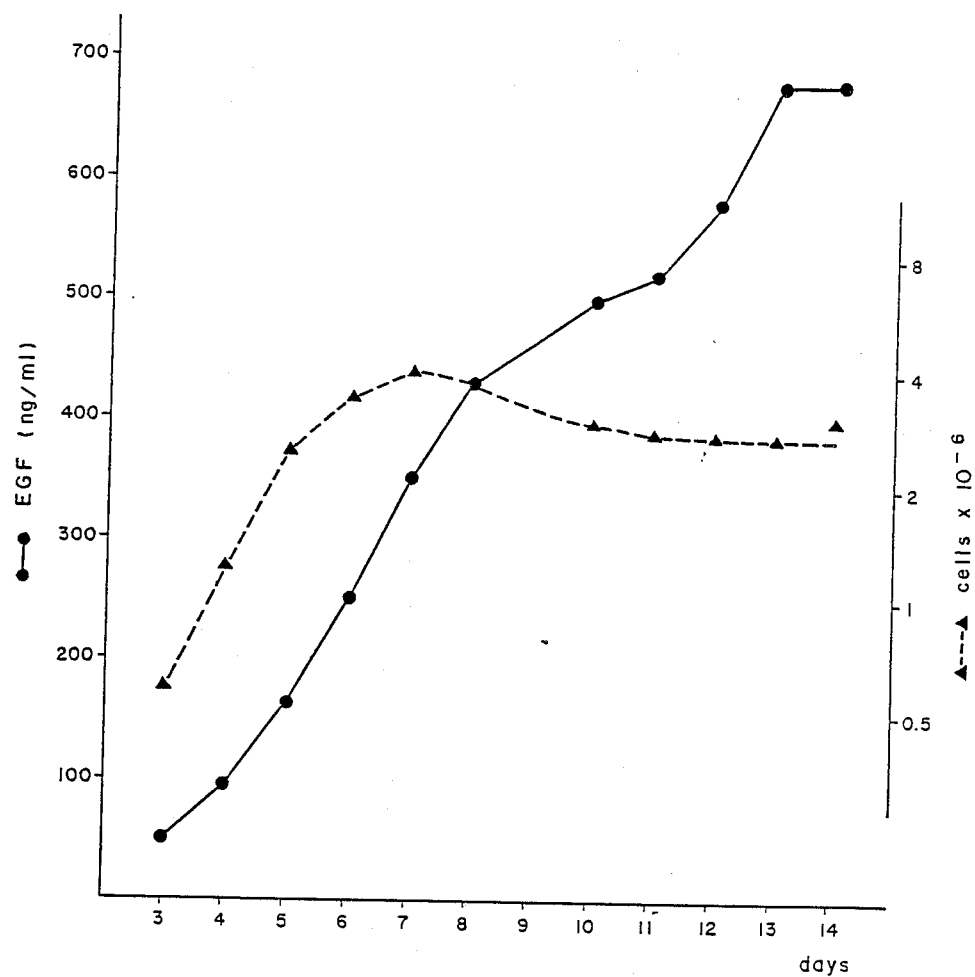
FIG. 5 shows the number of EGF-producing cells and the EGF concentration in the culture supernatant each as a function of time, obtained in Example 1.

Thus, Falcon dishes (3.5 cm in diameter) were each seeded with $5 \times 10^4$ LA9-IS11 EGF-2 cells and cultivation was conducted in 2 ml of DMEM medium containing 10% fetal calf serum in a $CO_2$ incubator maintained at 37° C. On the third day after start of the cultivation and thereafter, the cells were counted and the culture supernatant was assayed for EGF by the RAA method every day (FIG. 5). EGF was produced and accumulated with the cell multiplication and even after termination of the cell growth, the production of EGF continued to reach a maximum level of 680 ng/ml.

EXAMPLE 2

(Expression vectors for secretion of human IgE and animal cell transformants capable of producing human IgE)

(i) Construction of plasmids pTB541, pTB542, pTB543 and pTB544

Figure 6:
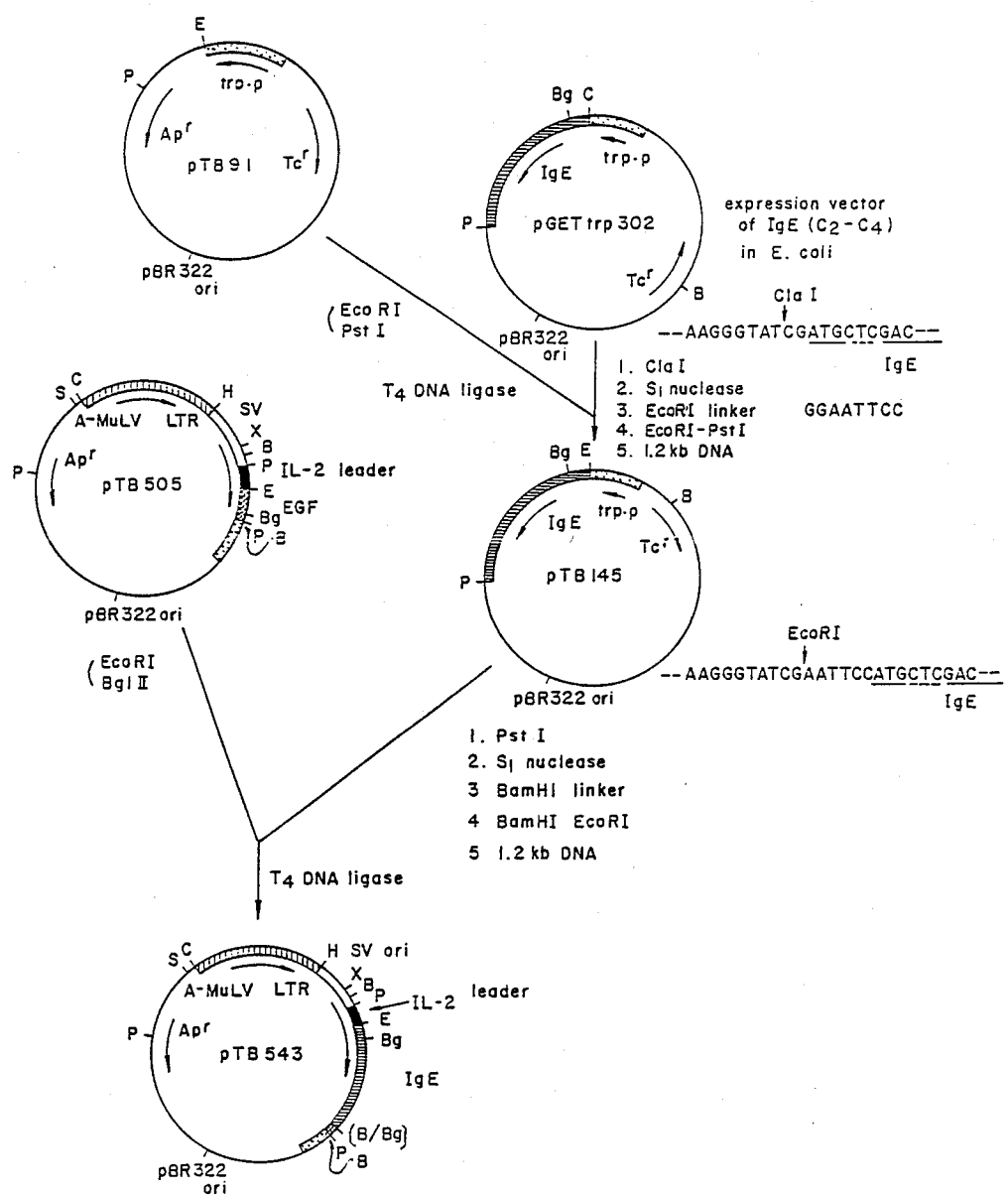
FIG. 6 shows the construction scheme for the plasmid pTB543.

The plasmid pGETtrp302 constructed such that the $C_2$–$C_4$ regions of the human immunoglobulin ε chain (IgE) can be expressed in *Escherichia coli* [Kurokawa et al., Nucleic Acids Res., 11: 3077–3085 (1983)] was cleaved at the ClaI site occurring between the trp promoter and the translation initiation codon ATG and, after rendering the cohesive ends blunt by $S_1$ nuclease treatment, joined with the EcoRI linker GGAATTCC After cleavage of the product with EcoRI and PstI, a 1.2 kb DNA fragment containing the IgE-encoding sequence was isolated. This 1.2 kb EcoRI-PstI DNA fragment was mixed with the EcoRI-PstI-cleaved plasmid pTB91 [Example 5 (ii) in the specification for Japanese Patent Application No. 210502/1984 (filed Oct. 9, 1984), which corresponds to European Patent Publication No. 177915] and pTB145 was constructed by T4 DNA ligase reaction. pTB145 was cleaved with PstI, the cohesive ends were rendered blunt with $S_1$ nuclease, the BamHI linker CCGGATCCGG was joined to the cleavage product, and the resulting product was cleaved by EcoRI-BamHI digestion to give a 1.2 kb EcoRI-BamHI DNA fragment. Separately, the plasmid pTB505 (EGF-secreting expression vector) constructed in Example 1 (ii) was cleaved with EcoRI-BglII to thereby remove a major portion of the EGF-encoding sequence and, in lieu of this portion, the 1.2 kb EcoRI-BamHI DNA fragment previously prepared from pTB145 and having the sequence coding for the $C_2$–$C_4$ region polypeptide of IgE was inserted. Thus was constructed pTB543. Thus, pTB543 is a recombinant plasmid having the IL-2 leader sequence, the sequence coding for the 11 amino acids on the N-terminus side of IL-2, the IgE-encoding sequence joined to said sequence encoding the 11 amino acids without causing any reading frame shift and, upstream from these sequences, the A-MuLV LTR and SV40 promoter regions as the promoters for gene expression in animal cells (FIG. 6).

In the same manner as above, pTB503 and pTB504 obtained in Example 1 (ii) were each cleaved with EcoRI-BglII, and pTB541 and pTB542 were constructed from the respective fragments and the above-mentioned pTB145-derived, IgE-encoding 1.2 kb BamHI-EcoRI DNA fragment. pTB541 has a structure such that the IL-2 leader sequence is joined to the IgE-encoding sequence and pTB542 has a structure such that the IL-2 leader sequence plus the sequence coding for the 4 amino acids on the N-terminus side of IL-2 is joined to the IgE-encoding sequence.

Furthermore, pTB544 having no IL-2 gene-derived leader sequence was constructed by replacing the EGF-encoding sequence in pTB506 described in Example 7 (i) in the specification for Japanese Patent Application No. 176976/1985 (filed Aug. 13, 1985), which corresponds to European Patent Publication No. 177,915, with the pTB145-derived IgE-encoding sequence in the same manner as above.

(ii) Transformation of animal cells

Eagle's MEM medium containing 10% fetal calf serum was placed in Falcon dishes (6 cm in diameter) and mouse TK-deficient L cells were cultivated overnight at 37° C. Thereafter, these cells ($7 \times 10^5$ cells/dish) were inoculated with a mixture of 0.2 µg of the plasmid pTK61 [PTK 61 is the product of cloning in pBR322 of a TK gene-containing 2 kb PvuII fragment [Proc Natl Acad. Sci. U.S.A., 78: 1441–1445 (1981)] of a plasmid isolated from *Escherichia coli* LE578 [Gene, 7: 335–342 (1979); gift of Dr. Enquist] carrying a recombinant plasmid obtained by cloning in pBR322 of a 3.5 kb BamHI DNA fragment containing the herpes simplex virus (HSV) TK gene] and 10 µg of one of the pTB541, pTB542, pTB543 and pTB544 DNAs according to the method of Graham et al. [Virology, 52: 456–467 (1973)]. After 4 hours of incubation at 37° C., the medium was replaced with a fresh portion and cultivation was conducted overnight. On the next day, the medium was replaced with HAT medium (MEM medium containing 15 µg/ml hypoxanthine, 1 µg/ml aminopterine, 5 µg/ml thymidine and 0.25 µg/ml glycine) containing 10% fetal calf serum and cultivation was continued at 37° C.

The cultivation was continued with medium exchange at 3- to 4-day intervals. Multiplication of those cells which had become TK+ resulted in colony formation in about 2–3 weeks.

(iii) Cloning of transformants and assay of IgE

The transformant cells obtained in Example 2 (ii) were cloned by the limited dilution method. After completion of the cloning, the cloned cells were cultivated in Eagle's MEM medium containing 10% fetal calf serum. The cloned cells separated were sowed into Linbro dishes and, when the cells were about 80% confluent, the medium in each well was replaced with a fresh 1-ml portion of the medium. On the third day, the culture supernatant was sampled for assay of IgE. At the same time, cells were scraped off with a rubber policeman and collected by centrifugation (2,000 rpm × 5 minutes). After addition of 0.3 ml of 10 mM Tris-HCl (pH 7.5) to the cells collected, the cells were disrupted by sonication (5 seconds × 2) and then subjected to centrifugation (20,000 rpm, 4° C., 3 minutes), and the supernatant thus obtained was assayed for IgE. The IgE activity determination was performed by the RIST method [Radioimmuno Sorbent test; Immunology, 14: 265 (1968)] using an IgE assay kit (IgE Test Shionogi, Shionogi & Co.).

From mouse L cells (TK+) transformed with the IgE expression vectors having the IL-2 leader sequence, namely pTB541, pTB542 and pTB543, there were obtained clones with which 50 U/ml or more of IgE could be detected in the culture supernatant. Among them, the pTB543-bearing transformant cell clone mouse L-IS11IgE-9 (IFO50056) was found to have produced and secreted 580 U/ml of IgE in the cutlure supernatant.

On the other hand, L cells transformed with pTB544 and having no IL-2 leader sequence gave only such clones that 15 U/ml, at best, of IgE was detected in the culture supernatant. Furthermore, the quantity of IgE detected in the cell extract was about 10–70 U/ml for pTB541-, pTB542- or pTB543-bearing transformant cells, whereas, for pTB544-bearing transformant cells, IgE was detected in the cell extract only in trace amounts (less than 2 U/ml). Thus, it was shown that transformant cells carrying the IL-2 leader sequence-containing IgE expression vectors can produce and secrete IgE in amounts at least 10 times greater as compared with vectors having no IL-2 leader sequence and that, in particular, pTB543-bearing transformant cells can produce and secrete IgE most abundantly. The results obtained are shown in Table 2.

TABLE 2

| Plasmid | Transformant cells | IgE Culture supernatant (U/ml) | IgE Cell extract (U/5 × $10^5$ cells) |
|---|---|---|---|
| pTB541 | L-IS0 IgE-4 | 68 | 32 |
|  | L-IS0 IgE-6 | 160 | 75 |
| pTB542 | L-IS4 IgE-7 | 78 | 75 |
|  | L-IS4 IgE-10 | 86 | 14 |
| pTB543 | L-IS11IgE-3 | 275 | 32 |
|  | L-IS11IgE-9 | 580 | 56 |
| pTB544 | L-IgE-1 | 10 | 1.5 |
|  | L-IgE-3 | 15 | 1.5 |

EXAMPLE 3

To Falcon dishes (6 cm in diameter) was poured mouse Balb/3T3 A31 cells [Int. J. Cancer, 12, 463 (1973)], the cells were cultivated in DMEM medium containing 10% fetal bovine serum at 37° C. overnight. These cells ($3 \times 10^5$ cells/dish) were cotransfected by inoculation with a mixture of 0.2 µg of plasmid pTB 6 described in Example 1 (vi) of Japanese Patent Laid-open No. 63282/1981, which corresponds to European Patent Publication No. 172619, and 10 µg of pTB 505 DNA, which was obtained in said Example 1, according to the method of Graham et al. [Virology, 52, 456–467 (1973)].

After cultivation at 37° C. for 4 hours, the medium was replaced with a fresh portions and cultivation was conducted overnight. On the next day, the medium was replaced with DMEM medium (containing 10% fetal bovine serum) containing 400 µg/ml of G418 (Geneticin, Gibco Inc.), and cultivation was continued at 37° C. The cultivation was continued with medium changes at 3 to 4 day intervals, whereby after 2 to 3 weeks, cells resistant to G418 multiplied to form colonies (ii) Cloning of transformants and assay of EGF The cloning of the transformants obtained in said item (i) and assay of EGF in the supernatant of the clones were carried out by the manner of Example 1 (iv). It was detected that 5 to 20 ng/ml of EGF is present in the supernatant of the cultivated medium of A31 cell transformants.

(iii) Multiplication of A31 cell transformants in a medium containing a slight amount of serum Comparison of the multiplications of transformant clone mouse A31-IS11EGF-2 (IFO 50093) whose production of EGF was detected in the supernatant of the cultivation, of the parent cell mouse Balb/3T3 A31 cell and of A31 cell to which mouse EGF (Collaborative Research, Inc.) has been added, was carried out.

DMEM medium containing 10% fetal calf serum was placed in Falcon dishes (3.5 cm in diameter) and $5 \times 10^4$ cells were inoculated, and the cells were cultivated in the medium which was replaced with DMEM medium containing 1% fetal calf serum. For a mouse EGF, the concentration of 10 ng/ml of it was used. After 3 days and 6 days, the medium was replaced with a fresh one and cultivation was continued and the number of cells was counted at timed intervals. The results are shown in FIG. 7.

Figure 7:
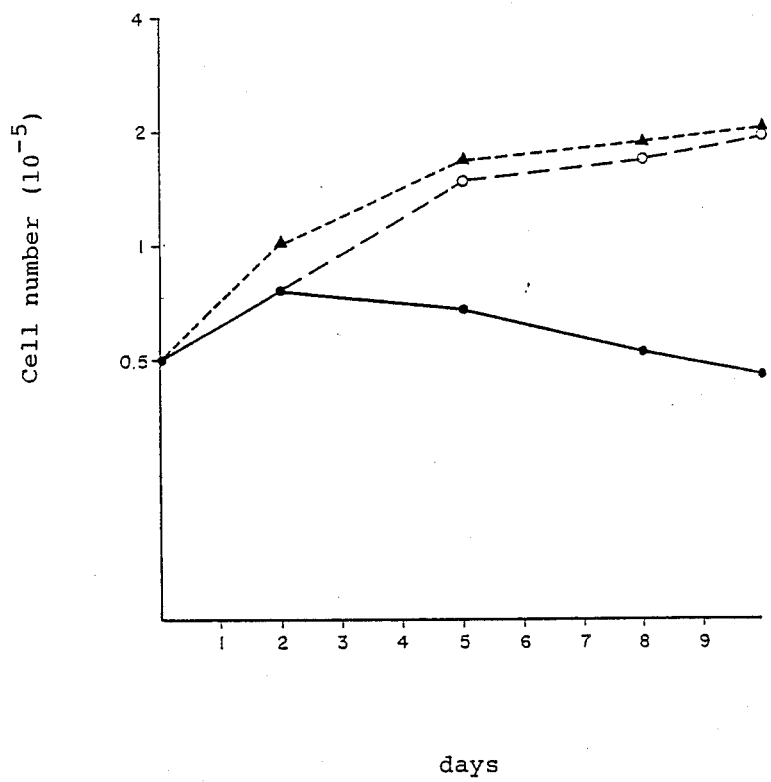
FIG. 7 shows the growth of EGF-producing cells, obtained in Example 3.

As seen in the FIG. 7, in the DMEM medium containing 1% fetal bovine serum, the parent A31 cells were not multiplied (this is shown by—●—), but the transformant A31-IS11EGF-2 cells (this is shown by—○—) produce EGF at a rate multiplied four(4) times that of the parent A31 cell after 7 to 9 days cultivation. This multiplication of the transformant is equivalent to the case where the parent A31 cell is cultivated in medium containing 10 ng/ml of mouse EGF (this is shown by — ▲ —).

What we claim is:

1. An expression vector which contains a DNA segment comprising:
   (a) a DNA sequence coding for a signal peptide of human interleukin-2 of the formula:

Met Tyr Arg Met Gln Leu Leu Ser Cys Ile Ala Leu Ser Leu Ala Leu Val Thr Asn Ser (b) a second DNA sequence coding for a different protein from the human interleukin-2 joined downstream of said signal peptide of human interleukin-2 encoding DNA sequence without causing any reading frame shaft, and
   (c) a promoter DNA sequence capable of functioning in an animal cell, wherein the promoter sequence is positioned upstream of the signal peptide of human interleukin-2 encoding DNA sequence.

2. An expression vector as claimed in claim 1, wherein the protein-encoding DNA sequence is selected from the group consisting of a hepatitis B virus gene, an immunoglobulin E gene, an immune interferon gene, a human epithelial cell growth factor gene and a human fibroblast growth factor gene.

3. A method for producing a DNA of an expression vector for use in an animal cell, which comprises constructing a DNA segment comprising
   (a) a DNA sequence coding for a signal peptide of human interleukin-2 of the formula:

Met Tyr Arg Met Gln Leu Leu Ser Cys Ile Ala Leu Ser Leu Ala Leu Val Thr Asn Ser (b) a DNA sequence coding for a different protein from the human interleukin-2, and
   (c) a promoter DNA sequence capable of functioning in an animal cell, in the order that the human interleukin-2 encoding DNA sequence is upstream of the protein-encoding DNA sequence and the promoter DNA is upstream of the signal peptide of human interleukin-2 encoding DNA sequence.

4. A method as claimed in claim 3, wherein the protein-encoding DNA sequence is selected from the group consisting of a hepatitis B virus gene, an immunoglobulin E gene, an immune interferon gene, a human epithelial cell growth factor gene and a human fibroblast growth factor gene.

5. The method claimed in claim 3, wherein the DNA sequence coding for the signal peptide of human interleukin-2 is GCACCTACTTCAAGTTCTACAAAGAAAACACAGCTACAACTGGAGCATTTACTGCTGGAT.

6. An animal cell line transformed with an expression vector for an animal cell, the expression vector which contains a DNA segment comprising:
   (a) a DNA sequence coding for a signal peptide of human interleukin-2 of the formula:

Met Tyr Arg Met Gln Leu Leu Ser Cys Ile Ala Leu Ser Leu Ala Leu Val Thr Asn Ser (b) a second DNA sequence coding for a different protein from the human interleukin-2 joined downstream of said signal peptide of human interleukin-2 encoding DNA sequence without causing any reading frame shaft, and
   (c) a promoter DNA sequence capable of functioning in an animal cell, wherein the promoter sequence is positioned upstream of the signal peptide of human interleukin-2 encoding DNA sequence.

7. An animal cell line as claimed in claim 6, wherein the protein-encoding DNA sequence is selected from the group consisting of a hepatitis B virus gene, an immunoglobulin E gene, an immune interferon gene, a human epithelial cell growth factor gene and a human fibroblast growth factor gene.

8. A method for producing an animal cell line, which comprises transforming an animal cell line with an expression vector which contains a DNA segment comprising:
   (a) a DNA sequence coding for a signal peptide of human interleukin-2 of the formula:

Met Tyr Arg Met Gln Leu Leu Ser Cys Ile Ala Leu Ser Leu Ala Leu Val Thr Asn Ser (b) a second DNA sequence coding for a different protein from the human interleukin-2 joined downstream of said signal peptide of human interleukin-2 encoding DNA sequence without causing any reading frame shaft, and
   (c) a promoter DNA sequence capable of functioning in an animal cell, wherein the promoter sequence is positioned upstream, of the signal peptide of human interleukin-2 encoding DNA sequence.

9. A method as claimed in claim 8, wherein the protein-encoding DNA sequence is selected from the group consisting of a hepatitis B virus gene, an immunoglobulin E gene, an immune interferon gene, a human epithelial cell growth factor gene and a human fibroblast growth factor gene.

10. A method of producing a protein, which comprises cultivating in a medium an animal cell transformed with an expression vector which contains a DNA segment comprising:
    (a) a DNA sequence coding for a signal peptide of human interleukin-2 of the formula:

Met Tyr Arg Met Gln Leu Leu Ser Cys Ile Ala Leu Ser Leu Ala Leu Val Thr Asn Ser (b) a second DNA sequence coding for a different protein from the human interleukin-2 joined downstream of said signal peptide of human interleukin-2 encoding DNA sequence without causing any reading frame shift, and
    (c) a promoter DNA sequence capable of functioning in an animal cell, wherein the promoter sequence is positioned upstream of the signal peptide of human interleukin-2 encoding DNA sequence.

11. A method as claimed in claim 10, wherein the protein-encoding DNA sequence is selected from the group consisting of a hepatitis B virus gene, an immunoglobulin E gene, an immune interferon gene, a human epithelial cell growth factor gene and a human fibroblast growth factor gene.

12. An expression vector as claimed in claim 1 wherein the protein encoding DNA sequence is selected from the group consisting of genes coding for physiologically active proteins, transforming growth factor, hormones; bacteria-derived antigenic proteins, and blood component proteins.

13. The method claimed in claim 10, wherein the DNA sequence coding for the signal peptide of human interleukin-2 is GCACCTACTTCAAGTTCTACAAAGAAAACACAGCTACAACTGGAGCATTTACTGCTGGAT.

* * * * *